United States Patent
Lu et al.

(10) Patent No.: US 12,194,054 B2
(45) Date of Patent: Jan. 14, 2025

(54) APPLICATION OF CHIDAMIDE IN COMBINATION WITH R-CHOP, AND DRUG COMBINATION

(71) Applicants: SHENZHEN CHIPSCREEN BIOSCIENCES CO., LTD., Guangdong (CN); RUI JIN HOSPITAL AFFILIATED TO SHANGHAI JIAO TONG UNIVERSITY SCHOOL OF MEDICINE, Shanghai (CN)

(72) Inventors: Xianping Lu, Shenzhen (CN); Weili Zhao, Shenzhen (CN); Xin Fu, Shenzhen (CN); Pengpeng Xu, Shenzhen (CN); Ting Liu, Shenzhen (CN)

(73) Assignees: SHENZHEN CHIPSCREEN BIOSCIENCES CO., LTD., Guangdong (CN); RUI JIN HOSPITAL AFFILIATED TO SHANGHAI JIAO TONG UNIVERSITY SCHOOL OF MEDICINE, Shanghai (CN)

(*) Notice: Subject to any disclaimer, the term of this patent is extended or adjusted under 35 U.S.C. 154(b) by 766 days.

(21) Appl. No.: 17/295,494

(22) PCT Filed: Nov. 18, 2019

(86) PCT No.: PCT/CN2019/119170
§ 371 (c)(1),
(2) Date: May 20, 2021

(87) PCT Pub. No.: WO2020/103788
PCT Pub. Date: May 28, 2020

(65) Prior Publication Data
US 2022/0016147 A1    Jan. 20, 2022

(30) Foreign Application Priority Data
Nov. 20, 2018  (CN) .......................... 201811394614.7

(51) Int. Cl.
| | |
|---|---|
| *A61P 35/00* | (2006.01) |
| *A61K 31/4406* | (2006.01) |
| *A61K 31/475* | (2006.01) |
| *A61K 31/573* | (2006.01) |
| *A61K 31/675* | (2006.01) |
| *A61K 31/704* | (2006.01) |
| *A61K 45/06* | (2006.01) |
| *C07K 16/28* | (2006.01) |

(52) U.S. Cl.
CPC ........ *A61K 31/704* (2013.01); *A61K 31/4406* (2013.01); *A61K 31/475* (2013.01); *A61K 31/573* (2013.01); *A61K 31/675* (2013.01); *A61K 45/06* (2013.01); *A61P 35/00* (2018.01); *C07K 16/2887* (2013.01)

(58) Field of Classification Search
CPC .............. A61K 31/704; A61K 31/4406; A61K 31/475; A61K 31/573; A61K 31/675; A61K 45/06; A61K 2039/505; A61K 39/3955; A61K 39/39558; A61K 39/395; A61K 2300/00; A61P 35/00; A61P 35/02; C07K 16/2887
See application file for complete search history.

(56) References Cited

U.S. PATENT DOCUMENTS

2015/0299126 A1    10/2015 Lu et al.

FOREIGN PATENT DOCUMENTS

| RU | 2603138 | 11/2016 | |
|---|---|---|---|
| WO | WO-2017197153 A1 * | 11/2017 | ........... A61K 31/167 |
| WO | 2018017858 A1 | 1/2018 | |

OTHER PUBLICATIONS

Zhao. NCT032753647, Chidamide Plus R-CHOP in Elderly DLBCL. ClinicalTrials.gov (Year: 2016).*
Shi, Y. Current status and progress of lymphoma management in China. International Journal of Hematology, 107(4), 405-412. https://doi.org/10.1007/s12185-018-2404-8 (Year: 2018).*
Cai et al. Long-term results of the R-CEOP90 in the treatment of young patients with chemotherapy-naïve diffuse large B cell lymphoma: A phase II study. Leukemia & Lymphoma/Leukemia and Lymphoma, 55(10), 2387-2388. https://doi.org/10.3109/10428194.2013.876632 (Year: 2014).*
Merli et al. Cyclophosphamide, doxorubicin, vincristine, prednisone and rituximab versus epirubicin, cyclophosphamide, vinblastine, prednisone and rituximab for the initial treatment of elderly "fit" patients with diffuse large B-cell lymphoma: results from the ANZINTER3 trial. Leukemia & Lymphoma. (Year: 2012).*
Yan et al. Chidamide ,Oral Subtype-Selective Histone Deacetylase Inhibitor (HDACI) Monotherapy Was Effective on the Patients with Relapsed or Refractory Extranodal Natural Killer (NK)/T-Cell Lymphoma. Blood, 130, 2797-2797. https://doi.org/10.1182/blood.v130.suppl_1.2797.2797 (Year: 2017).*
Extended European Search Report, EP Application No. 19887480.2, mailed Jun. 8, 2022 (7 pages).
Xu, Pengpeng et al., "A Phase II Study of Chidamide Plus R-Chop in Elderly Patients with Newly Diagnosed Diffuse Large B-Cell Lyphoma: An Interim Analysis", Blood, American Society of Hematology, vol. 130, p. 4126, Dec. 8, 2017 (2 pages).

(Continued)

*Primary Examiner* — Yih-Horng Shiao
*Assistant Examiner* — Hoi Yan Lee
(74) *Attorney, Agent, or Firm* — Ware, Fressola, Maguire & Barber LLP

(57) ABSTRACT

The present application provides an application of Chidamide in combination with R-CHOP in preparing a drug used for treating B-cell lymphoma, and also provides a drug comprising Chidamide and R-CHOP. Chidamide in combination with R-CHOP has a synergistic therapeutic effect on B-cell lymphoma.

4 Claims, No Drawings

(56) References Cited

OTHER PUBLICATIONS

Economopoulos T. et al., "CEOP-21 Versus CEOP-14 Chemotherapy With or Without Rituximab for the First-Line Treatment of Patients With Aggressive Lymphomas: Results of the HE22A99 Trial of the Hellenic Cooperative Oncology Group," The Cancer Journal, Sep.-Oct. 2007, vol. 13(5), pp. 327-334.
Lokesh K.N. et al., "Diffuse large B-cell lymphoma in elderly: Experience from a tertiary care oncology center in South India," South Asian J Cancer., Apr.-Jun. 2017, vol. 6(2), pp. 72-74.
Office Action and Search Report, RU Patent Application 2021114295/04(030398), Nov. 23, 2022 (17 pages).
Written Opinion and International Search Report from PCT/CN2019/119170, mailed Feb. 21, 2020 (14 pages).
Zhang Peipei "Mechanisms of Chidamide in Diffuse Large B-cell Lymphoma Cell Lines with Distinctive Proliferative Characteristics", Master's Dissertation of Zhengzhou University, May 1, 2016 (66 pages).
Li, Luke et al."Clinical Observation of R-CHOP Regimen in the Treatment of 36 Cases of Diffuse Large B-cell Lymphoma", Journal of Community Medicine, vol. 15, No. 12, Jun. 30, 2017 (3 pages).
Decision to Grant Patent, Japanese Patent Application No. 2021-551329, Apr. 24, 2024.

\* cited by examiner

APPLICATION OF CHIDAMIDE IN COMBINATION WITH R-CHOP, AND DRUG COMBINATION

The present application is a National Stage Entry of International Application No. PCT/CN2019/119170 filed Nov. 18, 2019, which claims the priority of the Chinese patent application that was filed with the Chinese Patent Office on Nov. 20, 2018, and has the application number of 201811394614.7 and the invention title of "Use of Chidamide combined with R-CHOP and combination drug thereof", and whose entire content is incorporated in the present application by reference.

TECHNICAL FIELD

The present application relates to the technical field of medicine, in particular to use of Chidamide combined with R-CHOP and a combination drug thereof.

BACKGROUND ART

B-cell lymphoma mainly includes diffuse large B-cell lymphoma (DLBCL), follicular lymphoma (FL), marginal zone B-cell lymphoma (MZL), mantle cell lymphoma (MCL) and so on. At present, the R-CHOP regimen of rituximab (R) combined with cyclophosphamide (CTX), adriamycin (ADR), vincristine (VCR) and prednisone (Pred) is used as standard first-line treatment regimen for diffuse large B cell lymphoma (DLBCL), and has achieved good long-term survival. Under the current conventional immunochemotherapy, ⅓ of patients still have no response to treatment or relapse, and there is still room for improvement in efficacy, such as changing the combination of conventional chemotherapies or adding targeted drugs. High-risk elderly DLBCL patients have poor efficacy for R-CHOP, with a CR rate of only about 70% and poor long-term survival, and the efficacy needs to be improved urgently.

SUMMARY OF THE DISCLOSURE

In view of this, the purpose of the present invention is to provide use of Chidamide combined with R-CHOP in the manufacture of a medicament for treating B-cell lymphoma and/or in the treatment of B-cell lymphoma. Therein, R-CHOP refers to a R-CHOP combination drug regimen in the field, that is, a combination drug regimen of rituximab (R) combined with cyclophosphamide (CTX), adriamycin or epirubicin (ADR/EPI), vincristine (VCR) and prednisone (Pred); in specific embodiments for carrying out the present invention, clinical trials were performed on diffuse large B-cell lymphoma as a specific disease to be treated.

Chidamide (Epidaza) is a subtype selective histone deacetylase (HDAC) inhibitor independently researched and developed in China, and is a new drug of class 1.1. The use of Chidamide for its first indication, monotherapy for relapsed or refractory peripheral T-cell lymphoma (PTCL), was approved by the China Food and Drug Administration (CFDA) on Dec. 23, 2014, and thus it is the first oral subtype selective HDAC inhibitor for this indication in the world approved for marketing. Chidamide mainly targets the subtypes 1, 2 and 3 of class I and the subtype 10 of class IIb of HDAC, and has a regulatory effect on abnormal epigenetic functions of tumors. It induces chromatin remodeling by inhibiting related HDAC subtypes to increase the acetylation level of chromatin histone, and thus leads to alterations in gene expression of multiple signaling pathways (i.e., epigenetic alterations), thereby inhibiting tumor cell cycle and inducing tumor cell apoptosis, and having overall regulatory activity on the body's cellular immunity, and inducing and enhancing the tumor killing effect mediated by natural killer cells (NK) and antigen-specific cytotoxic T cells (CTL). Chidamide also has functions such as inducing tumor stem cell differentiation and reversing the epithelial-mesenchymal phenotype transition (EMT) of tumor cells through epigenetic regulation mechanisms, thereby playing a potential role in restoring the sensitivity of drug-resistant tumor cells to drugs and inhibiting tumor metastasis and recurrence, etc.

The results of the phase I clinical trial of Chidamide showed that the effective remission rate of Chidamide in monotherapy of T-cell non-Hodgkin's malignant lymphoma was 80%, but for the 3 cases of B-cell non-Hodgkin's lymphoma patients as enrolled, one case showed progression of disease after treatment with Chidamide, and the other two showed stable disease without curative effect, so the above results indicated that Chidamide alone showed no effectiveness in the treatment of B-cell lymphoma.

However, it is unexpectedly found in the present invention that Chidamide combined with R-CHOP shows a synergistic effect in the treatment of diffuse large B-cell lymphoma, and especially has better efficacy for newly-treated, high-risk and elderly DLBCL patients. In the mid-term evaluation after using the combination drug strategy of the present invention, for a total of 31 evaluable patients, the CR rate was 90.3%, and the PR rate was 6.5%. In the final evaluation, for a total of 23 evaluable patients, the CR rate was 87% and the ORR was 100%. The results of this clinical trial showed that R-CHOP combined with Chidamide has a significantly improved efficacy in the treatment of newly-treated, elderly, high-risk diffuse large B-cell lymphoma as compared with R-CHOP regimen.

Based on the technical effects, the present application specifically provides a combination drug according to the proposed use, which comprises Chidamide, rituximab, cyclophosphamide, adriamycin or epirubicin, vincristine and prednisone in an effective dose for simultaneous, separate or sequential administration.

At the same time, the present application also provides a preparation for treating B-cell lymphoma, which uses the above combination drug as a main active ingredient, and is added with other active ingredients and/or preparation auxiliary materials that do not affect each other. The other active ingredients that do not affect each other can be an active ingredient for treating B-cell lymphoma, or an active ingredient for treating other diseases, or a combination of the two.

In addition, the present application also provides a method for treating B-cell lymphoma, comprising simultaneously, separately or sequentially administering Chidamide, rituximab, cyclophosphamide, adriamycin or epirubicin, vincristine and prednisone in an effective dose.

It can be seen from the above technical solutions that the present application proposes use of therapeutic regimen of Chidamide combined with R-CHOP that has a synergistic therapeutic effect on B-cell lymphoma, and verifies through clinical trials that the regimen of Chidamide combined with R-CHOP shows better effect in the treatment of diffuse large B-cell lymphoma as compared with R-CHOP regimen, and the use can treat patients with B-cell lymphoma more efficiently.

DETAILED DESCRIPTION

The present invention discloses use of Chidamide combined with R-CHOP and a combination drug thereof, and those skilled in the art can learn from the content herein and appropriately improve the process parameters to achieve the same. It should be particularly pointed out that all similar substitutions and modifications are obvious to those skilled in the art, and they are all deemed to be included in the present invention. The use of the present invention has been described through the preferred examples, and those skilled in the art can obviously make changes or appropriate alterations and combinations to the use described herein without departing from the content, spirit and scope of the present invention so as to implement and apply the technology of the present invention.

The following is a further description of the use of Chidamide combined with R-CHOP and combination drug thereof provided by the present invention.

Example 1: Prospective, Single-Arm, Open Phase II Trial of Chidamide Combined with R-CHOP Regimen in the Treatment of Newly-Treated, Elderly, High-Risk Diffuse Large B-Cell Lymphoma Test drugs: Chidamide tablets: off-white tablets, 5 mg/tablet. Produced by Shenzhen Chipscreen Biosciences Co., Ltd. R-CHOP combined chemotherapy drugs: rituximab (R) combined with cyclophosphamide (CTX), adriamycin or epirubicin (ADR/EPI), vincristine (VCR), prednisone (Pred).

Number of cases: It was planned that a total of 49 patients would be enrolled in this clinical trial.

Enrollment criteria: Patients must meet all of the following criteria so as to be enrolled.
1. Histopathologically diagnosed as diffuse large B-cell lymphoma, and CD20 positive;
2. Age: ≥61 years old, ≤75 years old;
3. ECOG physical status score: 0, 1 or 2 points;
4. No history of malignant tumor; and no other tumors occurred at the same time;
5. Patients with life expectancy of at least 6 months according to investigators' judgement;
6. Patients or their legal representatives must provide informed consent in written form before involving any special inspections or procedures of research.
7. International Prognostic Index (IPI): >1 point.

Therapeutic Regimen:
1. Names and dosages of the drugs to be studied were listed in the following table, and the administration methods in the following table were applied to patients:

TABLE 1

| Drug name | Dosage | Method of administration | Time of administration |
|---|---|---|---|
| R | 375 mg/m² | Intravenous bolus | Day 1 |
| CTX | 750 mg/m² | Intravenous bolus | Day 2 |
| EPI | 70 mg/m² | Intravenous bolus | Day 2 |
| VCR | 1.4 mg/m² | Intravenous bolus | Day 2 |
| Pred | 60 mg/m² | Oral | Days 2 to 6 |
| Chidamide | 20 mg/d | Oral | Days 1, 4, 8, 11 |
| Repeat time | | | Day 21 |

The subjects successively received 6 courses of R-CHOP regimen combined with Chidamide, once every 21 days. The subjects would unceasingly receive evaluation after the treatment was completed (the patients would enter the follow-up period described in the time and event table) until the end of the prescribed follow-up period (the total study duration was 3 years) or until the patients met the withdrawal criteria.

The necessary conditions for continued treatment are as follows, and if the following conditions were met, the next course of treatment would be carried out as planned:
(1) After myelosuppression, the neutrophil and platelet counts were in the rising stage;
(2) On the first day of the next course of treatment, blood neutrophils ≥1.0×10⁹/L, WBC≥3.0×10⁹/L;
(3) On the first day of the next course of treatment, platelet count ≥75×10⁹/L;

If not met, the next course of treatment should be delayed for 3-4 days, and the blood cell test should be repeated. If the above indicators were still not reached, the treatment would be delayed for another 3-4 days until the above-mentioned chemotherapy standards were met. If the treatment was delayed for more than 14 days and the standards were still not met, the patient would withdraw from the treatment and this would be recorded as an adverse event. The patient would be unceasingly followed up as required by the protocol.

The reduction standard of cytotoxic drugs:
(1) For those having neurotoxicity of grade 2 or higher, the VCR was reduced to 1 mg,
(2) When the neutrophil or platelet count was insufficient, the reduction of chemotherapy drugs should be considered. It could be implemented with reference to the following standards:
  (i) When the delay time of the next course of treatment was within 0 to 7 days: the original dosage should be maintained;
  (ii) When the delay time of the next course of treatment was within 8 to 14 days or grade 4 myelosuppression occurred in the last course of treatment, the dosage should be adjusted to:

| | |
|---|---|
| CTX | 75% |
| EPI | 75% |
| VCR | 100% |
| Pred | 100% |
| Chidamide | 100% |

Chidamide: If the disease had not progressed or there was no intolerable adverse reaction, it was recommended to continue the administration. During the entire treatment process, if grade 3-4 myelosuppression occurred, the administration should be suspended until the absolute value of neutrophils recovered to ≥1.5×10⁹/L and platelets recovered to ≥75.0×10⁹/L, and then the treatment with this product could be continued.

3. Combined medication and treatment:

In the first course of chemotherapy, for the patients with large tumor burden (huge mass or lactate dehydrogenase greater than or equal to 500 u/L) or PS equal to 2 or gastrointestinal NHL (prevention of gastrointestinal perforation), allopurinol and baking soda should be administrated, prednisone could be first orally administrated, and if necessary, chemotherapy could be administered in 2 days to prevent tumor lysis syndrome.

Granulocyte colony-stimulating factor (G-CSF): it could be used only when the therapist judged that it was necessary based on clinical prompts. The use of G-CSF should be recorded in the CRF table.

Concomitant treatment given due to adverse events, if it met the reporting standards, should also be reported, and the content should be filled out on the adverse event page of the CRF form. If necessary, patients should be given adequate supportive treatment, including infusion of whole blood and blood product, antibiotic treatment, antiemetic treatment, etc. Treatment reasons, and their dosage and treatment date should also be recorded in the CRF table.

For patients with huge masses, it was up to the investigator to decide whether radiation therapy should be given.

Clinical trial results: During the mid-term evaluation, for a total of 31 evaluable patients, the CR rate was 90.3% and the PR rate was 6.5%. During the final evaluation, for a total of 23 evaluable patients, the CR rate was 87%, and the ORR was 100%.

The results of this clinical trial showed that R-CHOP combined with Chidamide has a significantly improved efficacy in the treatment of newly-treated, elderly, high-risk diffuse large B-cell lymphoma as compared with R-CHOP regimen.

The above are only preferred embodiments of the present invention. It should be pointed out that for those of ordinary skill in the art, without departing from the principle of the present invention, several improvements and modifications can be made, and these improvements and modifications should also be regarded as falling into the protection scope of the present invention.

What is claimed is:

1. A method for initially treating elderly high risk diffuse large B-cell lymphoma in a subject in need thereof, the method is characterized by simultaneously, separately or sequentially administering Chidamide, rituximab, cyclophosphamide, epirubicin, vincristine and prednisone in an effective dose to obtain 100% overall response rate to the subject in accordance with the administration methods in the following table:

| Drug name | Dosage | Method of administration | Time of administration |
|---|---|---|---|
| R | 375 mg/m$^2$ | Intravenous bolus | Day 1 |
| CTX | 750 mg/m$^2$ | Intravenous bolus | Day 2 |
| EPI | 70 mg/m$^2$ | Intravenous bolus | Day 2 |
| VCR | 1.4 mg/m$^2$ | Intravenous bolus | Day 2 |
| Pred | 60 mg/m$^2$ | Oral | Days 2 to 6 |
| Chidamide | 20 mg/d | Oral | Days 1, 4, 8, 11 |
| Duration of 1 course | | | 21 days. |

2. The method according to claim 1, wherein the diffuse large B-cell lymphoma is CD20 positive.

3. The method according to claim 1, wherein the administration of Chidamide, rituximab, cyclophosphamide, epirubicin, vincristine and prednisone is repeated for 6 courses.

4. The method according to claim 1, wherein the age of subjects ranges from 61 to 75 years old.

* * * * *